United States Patent
Proksa

(10) Patent No.: US 9,977,139 B2
(45) Date of Patent: May 22, 2018

(54) DYNAMIC MODELING OF IMPERFECTIONS FOR PHOTON COUNTING DETECTORS

(71) Applicant: KONINKLIJKE PHILIPS N.V., Eindhoven (NL)

(72) Inventor: Roland Proksa, Neu Wulmstorf (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 686 days.

(21) Appl. No.: 14/408,125

(22) PCT Filed: Jun. 20, 2013

(86) PCT No.: PCT/IB2013/055075
§ 371 (c)(1),
(2) Date: Dec. 15, 2014

(87) PCT Pub. No.: WO2014/001984
PCT Pub. Date: Jan. 3, 2014

(65) Prior Publication Data
US 2015/0177395 A1 Jun. 25, 2015

Related U.S. Application Data

(60) Provisional application No. 61/666,001, filed on Jun. 29, 2012.

(51) Int. Cl.
| | | |
|---|---|---|
| G01T 7/00 | (2006.01) |
| A61B 6/00 | (2006.01) |
| A61B 6/03 | (2006.01) |
| G01T 1/24 | (2006.01) |
| G01T 1/17 | (2006.01) |

(52) U.S. Cl.
CPC ............... *G01T 7/005* (2013.01); *A61B 6/03* (2013.01); *A61B 6/4241* (2013.01); *G01T 1/17* (2013.01); *G01T 1/24* (2013.01)

(58) Field of Classification Search
CPC ......... A61B 6/4241; A61B 6/03; G01T 7/005; G01T 1/17; G01T 1/24
USPC ...................................................... 702/104
See application file for complete search history.

(56) References Cited

U.S. PATENT DOCUMENTS

| | | |
|---|---|---|
| 4,899,054 A | 2/1990 | Barfod |
| 5,315,506 A | 5/1994 | Wang et al. |
| 2007/0076842 A1 | 4/2007 | Tkaczyk et al. |
| 2008/0135789 A1* | 6/2008 | Du ................ A61B 6/032 250/580 |
| 2008/0253503 A1 | 10/2008 | Proksa |

FOREIGN PATENT DOCUMENTS

| | | |
|---|---|---|
| WO | 2004113951 A2 | 12/2004 |
| WO | 2011036624 A1 | 3/2011 |

OTHER PUBLICATIONS

Miyajima, et al., "Response of CdZnTe Detector in Measurement of Diagnostic X-ray Spectra", Proceedings of the Second International Workshop on EGS, Aug. 8-12, 2000.
(Continued)

*Primary Examiner* — Yoshihisa Ishizuka

(57) ABSTRACT

An apparatus (T) and method for correcting detector (104) measurement data for errors caused by imperfections in the detector (104) that effect the accuracy of the detector readings.

20 Claims, 3 Drawing Sheets

(56) References Cited

OTHER PUBLICATIONS

Guazzoni, et al., "High stability X-ray spectroscopy system with on-chip front-end in charge amplifier configuration", Nuclear Instruments and Methods in Physics Research A 512 (2003) 207-212.
Taguchi, et al., "An analytical model of the effects of pule pileup on the energy spectrum recorded by energy resolved photon counting x-ray detectors", Med. Phys. 37 (8) Aug. 2010.
Cammin et al: Compensation of Non-Linear Distortions in Photon-Counting Spectral CT: Deadtime Loss, Spectral Response, and Beam Hardening Effects; Proc. of SPIE, vol. 8313, pp. 83131t-83131T-7.
Roessl et al: "K-Edge Imaging in X-Ray Computed Tomography Using Multi-Bin Photon Counting Detectors"; Phys. Med. Biol. , vol. 52, 2007, pp. 4679-4696.

* cited by examiner

DYNAMIC MODELING OF IMPERFECTIONS FOR PHOTON COUNTING DETECTORS

CROSS-REFERENCE TO PRIOR APPLICATIONS

This application is the U.S. National Phase application under 35 U.S.C. § 371 of International Application No. PCT/IB2013/055075, filed on Jun. 20, 2013, which claims the benefit of U.S. Provisional Patent Application No. 61/666,001 filed on Jun. 29, 2012. These applications are hereby incorporated by reference in their entirety herein.

FIELD OF THE INVENTION

The present invention relates to a detector data processing apparatus, to a detector data processing method, to an X-ray imaging system, to a computer program element and to a computer readable medium.

BACKGROUND OF THE INVENTION

It has been observed that using energy dispersive photon counting detectors in computed tomography (CT) imaging tasks sometimes leads to incorrect detector readings because of imperfections in the detector. Errors in detector measurements can lead to artifacts in images reconstructed therefrom. Some detector imperfections can even change the detector's behavior during a CT scan.

US2008/0253503 describes a spectral CT system including a detector.

SUMMARY OF THE INVENTION

There may therefore be a need for an apparatus to process detector readings in a different way. The object of the present invention is solved by the subject matter of the independent claims where further embodiments are incorporated in the dependent claims. It should be noted that the following described aspect of the invention equally apply to the detector data processing method, to the X-ray imaging system, to the computer element and to the computer readable medium.

According to one aspect of the present invention is provided a detector data processing apparatus comprising:

an input interface for receiving measurement data detected by a multi-bin radiation energy detector comprising a number of detector bins, the data detected during a measurement of radiation previously interacting with an object of interest, the data detected by the detector during a measurement operation for an M ($\geq 2$)-fold material decomposition with M less than the number (B$\geq 3$) of detector bins;

a data transformer configured to transform the detected measurement data into radiation attenuation data whilst correcting for a measurement error caused by the detector changing its responsiveness during the measurement operation, the transformer using a radiation-matter interaction model including:

i) a data parameter that is a parameter for the data detected by the detector bins;
ii) M-fold material decomposition variables; and
iii) a variable for a detector state that causes the change in the detector's responsiveness;

the transformer configured to solve the model for the material decomposition variables alongside the detector state variable thereby effecting the correction;

an output unit configured to output the solved material decomposition variables as the corrected radiation attenuation data.

According to one embodiment, the operation of the transformer includes outputting the solved detector state variable. This allows analyzing detector characteristics for example to compare different lots of detectors as provided by a manufacturer.

In M-fold material decomposition, each point of the object is assumed a priori to be a mixture of M basis materials. The effect of the x-ray attenuation experienced at that material point is decomposable into a linear combination of the attenuation effect for each of the M ($\geq 2$) basis materials for this M-fold material decomposition. The M-fold material decomposition describes for each material the interaction or attenuation of the radiation as the same passes through the object and therefore said material. The M-fold material decomposition allows "spectral CT", so images can be constructed each showing a distribution of only one of the M basis materials. In this way one can tell for example calcium deposits from a remaining bone structure. A conventional CT imaging apparatus would remain "blind" for such a resolution into calcium and non-calcium attenuation contributions. The number M of different basis materials is assumed fixed throughout the imaging operation and it is understood that M is any natural number larger than or equal to 2 that best suits modeling needs of a specific object for which an M-fold decomposition is sought. According to one embodiment the apparatus allows a user to adjust M as desired. The state variable may be a time varying scalar value or time varying vector quantity with more than one component. The material decomposition variables each describing the radiation attenuation caused by the respective material may be consolidated into a single multi-dimensional ($\geq 2$) variable. Whatever the representation, the individual contributions of the different materials must be distinguishable.

According to one embodiment, the model is defined by a system of integral equations each including an integral over the energy spectrum of the radiation with each energy spectrum element weighted by an attenuation factor, each equation including at least one of the data parameter and/or the detector state variable and/or the material decomposition variables.

According to one embodiment, the model is defined by a joint probability mass function representing a probability for the detector bins registering a particular measurement event, the joint probability mass function including at least one of the data parameter and/or the state variable and/or the material decomposition variables.

According to one embodiment, the operation of the transformer includes solving the joint probability mass function for the material decomposition variables and/or the state variable by using a maximum-likelihood approach.

According to one embodiment, the solving for the state variable and the material decomposition includes restricting the solution space for the state to functions satisfying a regularization condition wherein the condition is enforced by a penalty function.

According to one embodiment, the penalty function is quadratic.

According to one embodiment, the joint probability mass function is of the Poison type.

According to one embodiment, the detector's state represents a changing persistent current in a primary converter of the detector wherein the detector is of the photon counting type. In this embodiment, the changing persistent current changes the energy sensitivity of an energy responsive-(function) of the detector.

According to one embodiment, the detector's state represents a polarization of the primary convertor which causes a lower charge collection efficiency.

In other words the apparatus as proposed herein corrects detector readings for errors caused by imperfections or dynamic effects in the detector that lead to said incorrect readings. The underlying attenuation model that models the examined object with M material decomposition variables is extended by a state variable (which is either a scalar or a vector) to also model the dynamics or change over time of a detector property whose change causes the incorrect readings. The detector property is dynamic because it may change during the very measurement operation and the transformer as proposed herein allows accounting for this change in the correction. Because there are more detector bins B than the M variables to model the M-fold material decomposition for the examined object, there is a bin "redundancy". The material decomposition variables used in the attenuation model are extended by harnessing this redundancy. This allows increasing the number of variables in a meaningful way. The so extended set of variables including both, the dynamic detector state variable and the material specific decomposition variable (as referred to as attenuation line integrals or "attenuation coefficients") are used to explain the actually observed bin counts. The proposed apparatus allows therefore accounting for a change in the detector's behavior that occurs during the measurement operation, that is, for example during a (spectral) CT scan using said detector.

According to one embodiment if the number (that is their dimensionality) of variables so extended is still less than the number of energy bins, a statistical approach as indicted above is used to estimate the attenuation coefficients.

The proposed apparatus and method can be used in particular for photon counting detectors in spectral CT.

BRIEF DESCRIPTION OF THE DRAWINGS

Exemplary embodiments of the invention will now be described with reference to the following drawings wherein.

DETAILED DESCRIPTION OF EMBODIMENTS

Figure 1:
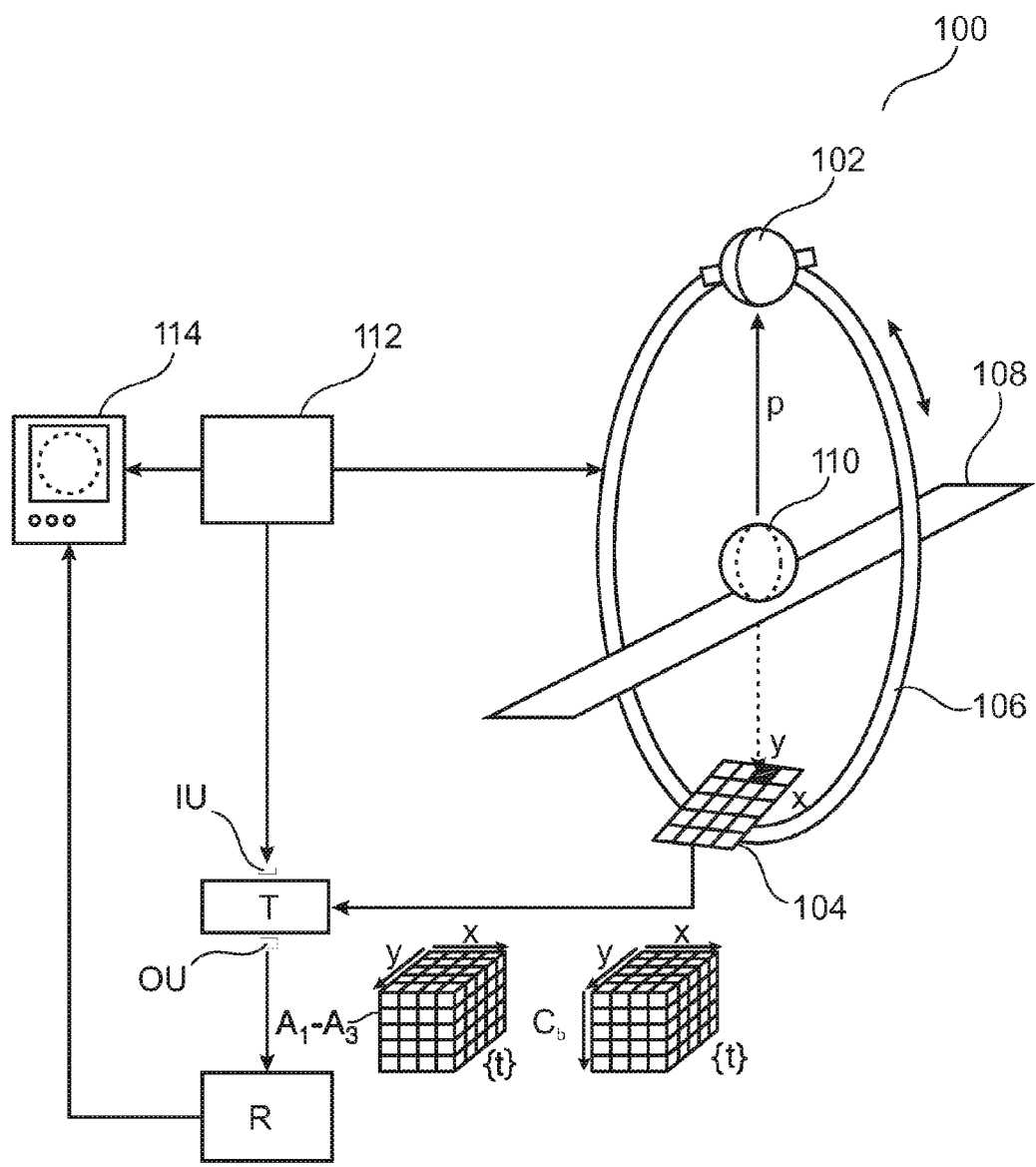
FIG. 1 shows a block diagram of a CT imaging system.

FIG. 1 shows a CT imaging apparatus 100. A rigid rotatable gantry 106 includes in an opposing spatial relationship an x-ray tube 102 and a detector 104. An object 110, such as a patient, is disposed on an examination table 108. Gantry 106 is essentially doughnut shaped and table 108 is introduced into the opening thereof such that a region of interest of object 110 is arranged substantially in the center of a circle formed by rotation of x-ray tube 102 and detector 104 in an image plane. Gantry 106 is driven by a suitable motor (not shown). The motor effects rotation of gantry 106 around the object 110 during the CT image acquisition period. The image plane is changeable by movement of the examination table in the gantry opening.

The operation of CT imaging apparatus 100 is controlled by an operator from a console 112. The console 112 is a computer unit that allows the operator to control the rotation as well as exposures to acquire individual detector readings by projecting an X-ray beam p emanating from X-ray tube 102 onto detector 104 after the beam's passage through the object 110. More specifically, X-ray beam p is attenuated by matter in said object 110 and it is the so attenuated beam (shown as a dashed line in FIG. 1) that is then incident on one or more detector cells 104a-c which together form the detector 104. Detector cells 104a-c are arranged in a two dimensional grid x,y as shown in FIG. 1. As will be explained in more detail below with reference to FIG. 2, the attenuated x-ray beam indecent on a respective detector cell 104a-c triggers an electric signal in that cell. Said electric signal is then translated into a digital value ("reading") associated with respective detector cell's grid position x,y.

As gantry 106 rotates around the object, a plurality of different projection images or detector readings ("bin counts") are acquired along different projection directions a defined by rotation angle α of the line joining detector 104 and x-ray tube 102. The plurality of readings indexed by their acquisition time, projection angle, image plane (z-coordinate) and detector cell 104a-c position is then consolidated into a high dimensional data block of detector readings.

Said block of detector readings is then forwarded via a suitably configured input unit (IU) to a detector data transformer T whose operation will be explained in more detail below.

The so transformed data reading block is then forwarded to a reconstructor R which processes the readings block by known back projection algorithms to generate one or more cross-section images ("slices") for each image plane. Each slice includes image information on inside structures of the object at the respective image (or slice) plane. The sequence of slices generated in this manner forms a 3D volume image.

Using suitable renderer or viewer software that runs on console 112, the user can then view the slice images on monitor 114.

As proposed herein data transformer T transforms the block of detector readings into a transformed data block thereby correcting or accounting for imperfections in the detector cells. It is this transformed and error corrected detector readings block that is then forwarded via suitably configured (output unit) OU to reconstructor R because using the erroneous detector data for the back projection may lead to image artifacts in the reconstructed slice images.

According to one embodiment, transformer T is arranged as a module in a data acquisition unit DAS (not shown) of the imaging apparatus 100. Although transformer T, input unit IU, output unit OU and console 112 are shown as separate components in FIG. 1, this is partly for ease of exposition. In one embodiment said transformer T indeed runs in a distributed architecture and is connected in a suitable communication network with console 112 as schematically shown in FIG. 1. In one embodiment data acquisition unit DAS and data transformer T (whether or not included in data acquisition unit DAS) may run as software routines on computer console 112. Transformer T may also be arranged as a dedicated FPGA or as hardwired standalone chip. Transformer T may be programmed in a suitable scientific computing platform such as Matlab® or Simulink® and then translated into C++ or C routines maintained in a library and linked when called on by computer console 112 or data acquisition system DAS.

Figure 2:
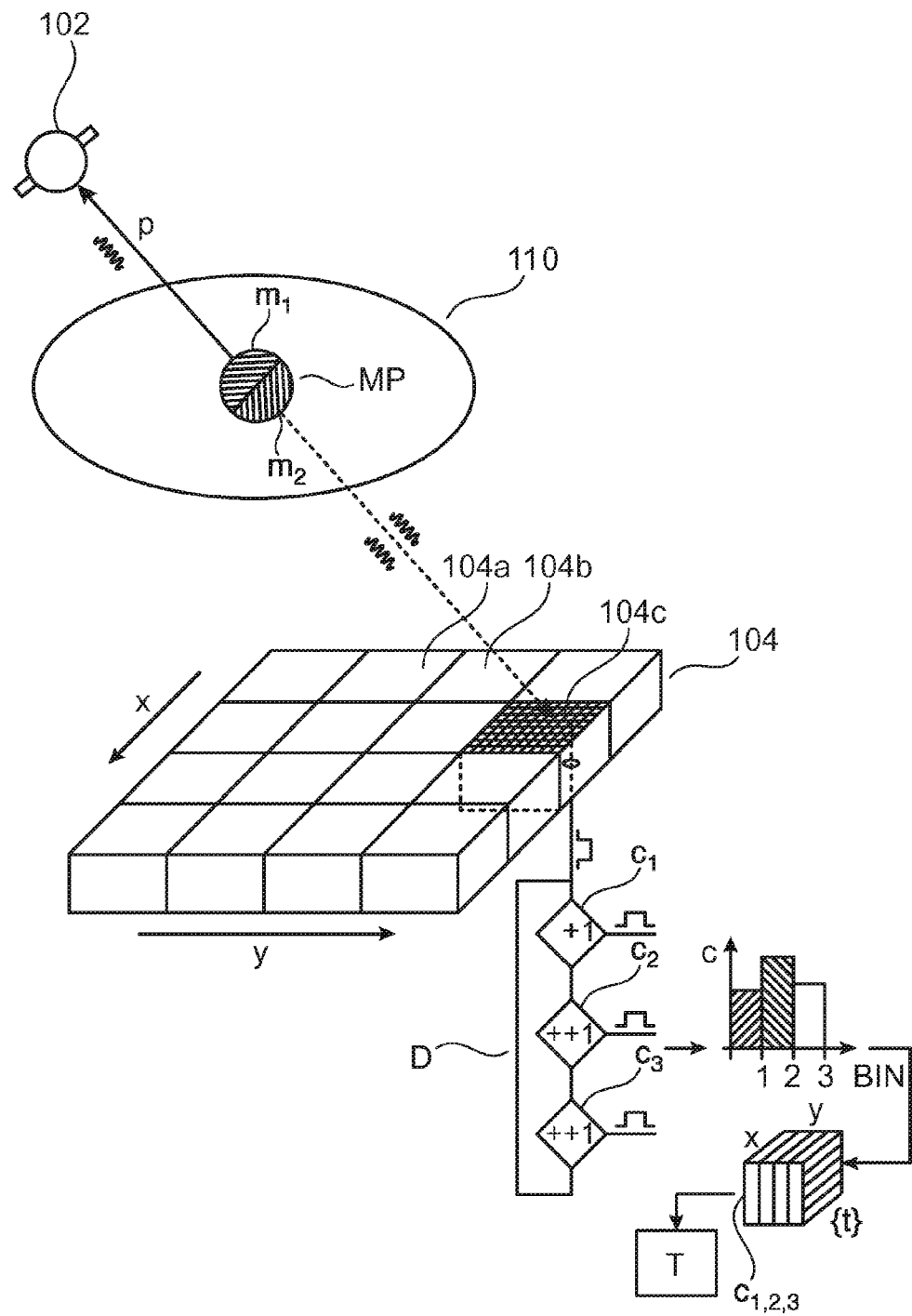
FIG. 2 shows a more detailed view on a detector used in the system of FIG. 1.

With reference to FIG. 2 the operation during image acquisition of detector 104 is now explained in more detail. FIG. 2 shows in more detail the detector cells 104 a-c and their interaction with beam p.

FIG. 2 shows in more detail passage of x-ray beam p from x-ray source 102 through the object 110 and its impacting at a detector cell, for example 104 c, of detector 104. Each point MP of object 110 is assumed to be a mixture of different materials $m_1$, $m_2$ as schematically indicted in FIG. 1. In other words, for the purpose of M-fold material decomposition measurement operation, the number of basis materials in FIG. 2 is M=2 but it is understood that is just an example and any M≥2 may be used depending on the specifics of the object 110 examined and the detector used. X-ray beam p interacts differently with different materials $m_1$, $m_2$ resulting in different types of radiation and different degrees of attenuation, e.g. the denser the material $m_1$, $m_2$ the higher the attenuation. The attenuated X-ray beam is polychromatic, meaning it has a spectrum made up of spectral components at different frequencies, with each spectral component largely characteristic to respective materials $m_1$, $m_2$. Imaging apparatus 100 is a spectral CT imaging apparatus and therefore operates in a material discriminatory mode to determine from the detected readings the material composition of the object 110 under examination. To this end, detector 104 is of the photon counting type. Photon counting detectors count each individual incident X-ray beam p and measure each photon's energy. Photon counting enables spectral CT using sub-ranges or bins (≥3) of the spectrum in order to form images based on the analysis of the spectral-signature of tissues. The slice images can then be reconstructed to show, separately or combined, the distribution per slice of each of the materials $m_1$ or $m_2$. Each cell 104a-c in a photon counter includes an upper and lower substrate arranged in the direction of the impacting X-ray beam with a primary convertor disposed between same. Each photon incident on detector cell 104c causes an electric current to flow between the two substrates and through the primary convertor. The current is in the form of an electrical pulse with a pulse height characteristic of the energy of the photon and thus characteristic of the respective material $m_1$-$m_2$.

The energy pulse so generated is intercepted by a suitable discriminatory circuitry D. Circuitry D is essentially a system of counters C1-C3 with each counter responsive only to the respective characteristic pulse bin energy level.

The output for each detector cell via said circuitry is essentially a histogram recording a number of registrations or hits at a specific energy level. The number of different energy levels into which cell is capable of resolving an incident energy quantum into is the number of energy bins. For example the detector in FIG. 2 has three energy bins.

Some energy dispersive photon counting detectors have more energy bins than independent free parameters for a measurement task, that is, more energy bins than material decomposition variables $A_1$-$A_M$ each representing the attenuation caused by the respective material. For example, in a CT imaging system the energy dependent absorption may be modeled with the photo electric effect and Compton scattering because an attenuation coefficient of most materials found in the body can be decomposed into a photoelectric component which is strongly dependent on a material's atomic number and a Compton-scattering component which is primarily dependent on density. If the detector has more than 3 bins, the measurements provide redundancy. In general, each material $m_1$, $m_2$ used for the decomposition affects the count in each of the bins because of cross-interaction effects and the detector's changing behavior during the CT measurement operation.

The apparatus proposed herein utilizes this redundancy and includes the dynamic detector imperfections in effect during the measurement into its modeling of the attenuation.

In one embodiment, the dynamic detector imperfection is a slowly varying current in the primary converter, sometimes called persistent current. Said persistent current is superimposed to charge pulses actually caused by detected photons. In other words, the pulse heights that are supposed to be characteristic to energy of the incident photons are overestimated by detector 104. Unfortunately this pulse "offset" cannot easily be measured and causes significant signal degradation in the detector readings.

Transformer T operates on a model for the detector beam interaction. Said model relates the material decomposition variable or "attenuation coefficients" $A_1$-$A_M$ to the observed photon counting events and detector state variable $\vec{x}(t)$ describing the time dynamics of said state.

Assuming for a moment that there are no detector imperfections one may model the detector measurements according to the following system of equations or mathematical equivalents thereof:

$$C_b = \int R(E) S_b(E) e^{-\sum_{m=1}^{M} f_m(E) A_m} dE, \quad m=1 \ldots M,$$
$$b=1 \ldots B$$

with:
R(E) the emission spectrum of the x-ray source,
$S_b(E)$ the spectral sensitivity of bin b,
M the number of basis materials,
$f_m(E)$ the energy dependence of basis material m,
$A_m$ (material decomposition variable) the line integral of material m through the object 110 along a projection direction given by the gantry (or X-ray tube) position,
$C_b$ the measured or registered number of counts in bin b=1 . . . B, given the above model.

The emission spectrum R is modeled according to known theoretical models that describe the spectrum of the X-ray radiation as emitted by x-ray tube 102. The emission spectrum includes Bremsstrahlung spectrum and the spectrum characteristic to the x-ray tube 102 used. The emitted spectrum is then multiplied by the absorption contributions of the respective base materials m=$m_1$, $m_2$ through which the X-ray is passing.

The spectral sensitivities $S_b$ can be obtained by either calibration measurements of the detector or by using known theoretical detector models. According to one embodiment, the spectral sensitivities are in general combinations of perturbed Heaviside functions with their 0-to-1 transitions smoothed.

The energy dependency $f_m$ is based on theoretical models for the type of radiation caused by the respective basis materials $m_1$, $m_2$. In one embodiment, the material $m_1$ is assumed to cause photo effect attenuation and $m_2$ is assumed to cause Compton scattering. The photo effect attenuation can be modeled as $e^-$ and the Compton scattering can be modeled according to the integrated Klein-Nishima formula.

Material decomposition or discrimination can be expressed as a task to estimate unknowns $A_m$ using measurements $C_{b, \ldots, B}$ in the above set of equations. Each attenuation coefficient $A_m$ describes a contribution of each of the material to the spectral absorption with energy dependence $f_m$. Because of the bin redundancy, that is B>M, the model is over-determined. In yet other words, the minimum number of variable of coefficients $A_m$ that are required to describe the attenuation contributions of the respective materials is less than the number of detector bins B and B is at least 3.

Now, according to one embodiment, there are dynamic effects operating in the detector 104 that change the response or cause another accuracy compromising behavior of the detector during the image acquisition period. Detector dynamics may be modeled by a possibly multi-dimensional variable $\vec{x}(t)$ hereinafter referred to as the (dynamic) detector state vector.

Assuming the changed bin sensitivity is known, the previous model is extended according to one embodiment as:

$$C_b = \int R(E)\tilde{S}_b(E,\vec{x}(t))e^{-\sum_{m=1}^{M} f_m(E)A_m} dE \quad (1)$$

The above set of equations (1) define a transformation T: $C_b \to (A_1, \ldots, A_m, \vec{x}(t))$ which is implemented by transformer T with $\tilde{S}_b(E,\vec{x}(t))$ the effective spectral sensitivity which is now a function of the detector state. Transformer T reads in the detector readings or bin counts $C_b$ of the data block and outputs after the transformation an error corrected set of material decomposition variables $A_1$-$A_m$. In one embodiment the computed values of the detector state $\vec{x}(t)$ may also be output.

There are still $b=1 \ldots B$ equations but now the set of variables $A_1$-$A_M$ to be solved for has been extended by the state vector $\vec{x}(t)$ to $M+\dim[\vec{x}(t)]$ where $\dim[.]$ is the cardinality or "length" of the state vector, $\vec{x}(t)=(x_1(t), \ldots x_K(t))$, $\dim[\vec{x}(t)]=K$, $x_i(t)$ the $K\geq 1$ components of state vector $\vec{x}(t)$. In other words, there is now a "virtual" extension of the material decomposition (attenuation) variables $A_1$-$A_m$ by the components of the detector state $\vec{x}(t)$. Said extended decomposition $A_1, \ldots, A_M, x_1, \ldots, x_K$, when solved together, will not only yield the detector state, but it automatically provides an improved estimation of $A_m$ because the actual state of the detector is taken into account thereby correcting for the dynamic effect and transforming the detector readings $C_b$ into error corrected attenuation coefficients $A_1$-$A_m$. In other words, the absorption model is fitted to the actual behavior of the detector used.

After the extension of the set of material decomposition variables there are two possibilities.

In case $\dim[\vec{x}(t)]+M=B$, the model will yield exactly one solution.

In case $\dim[\vec{x}(t)]+M<B$, there still is an over-determined system of equations. According to one embodiment a statistical approach is used by transformer T incorporating a noise model for detector 104. According to one embodiment an underlying Poisson process is assumed.

The corresponding likelihood function of a Poisson probability mass function is then defined by:

$$P(d_1, \ldots, d_B | C_1(A_\alpha, \vec{x}(t)), \ldots, C_B(A_\alpha, \vec{x}(t))) = \prod_{b=1}^{B} \frac{[C_b(A_\alpha, \vec{x}(t))]^{d_b}}{d_b!} e^{-C_b(A_\alpha, \vec{x}(t))}$$

for a given measurement $d_1, \ldots, d_B$ and $A_\alpha = (A_1, \ldots, A_M)$.

The negative log likelihood is $$L(d_1, \ldots, d_B | C_1(A_\alpha, \vec{x}(t)), \ldots, C_B(A_\alpha, \vec{x}(t))) \cong \sum_{b=1}^{B} C_b(A_\alpha, \vec{x}(t)) - d_b \ln C_b(A_\alpha, \vec{x}(t)) \quad (2)$$

Next, appropriate numerical methods are used to find a set $\{A_\alpha, \vec{x}(t)\}$ that minimizes L.

According to one embodiment, said solution may be improved by enforcing regularization in the function space of the solutions to L.

According to one embodiment, the detector state is the persistent current in the primary convertor so $\vec{x}(t)$ is assumed to be a slow varying function over time t. In this case the regularized objective function becomes minimal at $$\{A_\alpha, \vec{x}(t)\} = \underset{A_\alpha, \vec{x}(t)}{\operatorname{argmin}}[L(d_1, \ldots, d_B, A_\alpha, \vec{x}(t) + \beta P(\vec{x}(t))]$$

with $\beta$ being the regularization strength and P being a penalty function. The regularization strength is a user-adjustable variable that allows "trimming" or fine-tuning the effect of the penalty function on the minimization. A value larger than unity biases the minimization to particularly slow varying functions. However in some cases this may yield a next to constant function as the only solutions, which may be unrealistic. Choosing $\beta$ less than unity may then also admit slow varying functions other than constant functions as solutions. In other words regularization strength $\beta$ allows for "reality checking" the algorithm. According to one embodiment, the apparatus allows the user to change the regularization strength.

According to one embodiment, the detector state is the slow varying persistent current, so the detector state $\vec{x}(t) \equiv I_{Persistent}(t)$. This current affects the bin sensitivity with a related energy offset so pulses are registered in sensor 104 as "bogus" pulses with a higher energy as compared to the actual pulse height.

According to one embodiment, the effective bin sensitivity is:

$$\tilde{S}_b(E, \vec{x}(t)) = S_b(E + c\vec{x}(t)),$$

wherein c is a conversion factor to effect conversion from detector current to energy as given by the detector's electronics. In other words, the bin's effective sensitivity is shifted by $c\vec{x}(t)$ as compared to the assumed sensitivity $S_b$.

It is assumed in the above that the detector's energy response is shift-invariant so is independent of the energy E. If this is not the case, a more complex model may be used, for example a moving average stochastic processes.

According to one embodiment, the penalty function is a quadratic function $$P(\vec{x}(t)) = \left\| \frac{\vec{x}(t) - \vec{x}(t-1)}{\vec{x}_{Ref}} \right\|^2,$$

where $\vec{x}(t-1)$ represents the state at the previous measurement and $\vec{x}_{Ref}$ is to normalize P. In other words, solutions that are not slowly varying attract a higher penalty that grows with the square of said variation.

According to one embodiment, the detector state is the detector's 104 polarization. This is caused by trapped charges in the primary convertor and changes the collection efficiency of the detector 104 used. In this case $$\vec{x}(t) \equiv p(t); \text{ and}$$
$$\tilde{S}_b(E, \vec{x}(t)) = S_b(Ep(t))$$

In this model p(t) describes a relative energy scaling factor to reflect varying charge collection efficiency. For example, if the charge collection efficiency is reduced by a factor of 2 relative to a nominal state, the related energy scaling in the detector response is modeled by p(t)=2.

According to one embodiment, the model is extended to account for both of the previous dynamic detectors states of i) the detector's persistent current, and ii) the detector's polarization. In one embodiment this is modeled simultaneously for both states.

The models as used herein and as referred to above are assumed to be available in a suitably well-conditioned discretized form (by discretizing the energy axis E) to allow digital processing by transformer T with sufficient numerical stability.

In the above two embodiments where the detector state is either the persistent current $I_{Persistent}(t)$ or the polarization p(t), $\dim[\vec{x}(t)]=1$ so the variable set $A_m$ to solve for is extended by one. In the embodiment, where both, the persistent current $I_{Persistent}(t)$ and the polarization p(t) is taken into account, $\vec{x}(t)=(I_{Persistent}(t), p(t))$, so $\dim[\vec{x}(t)]=2$ and the variable set $A_m$ to solve for is extended by two to $(A_m, I_{Persistent}(t), p(t))$.

Transformer T carries out the above computations to solve equation (1) for $(A_m, \vec{x}(t))$ for each time instant t and associates the so computed and error corrected $A_m$ values with their respective time index. For example, if the system still happens to be over-determined, a maximum likelihood estimation is carried out by Transformer T for each instant t according to equation (2). In this manner, the error corrected data block is build up and passed to reconstructor R. It is understood that it is in general also the basis material components that have a time and/or projection direction a and/or z-component dependency. Therefore, $m_1(t, \alpha, z)$, $m_2(t, \alpha, z)$ is different for each t in the above computations because assumed material composition is in general different when said object 110 is viewed along different projection directions as gantry 106 rotates around said object 110 and/or a different imaging plane (z-component) is selected by advancing table 108 through gantry 106.

Figure 3:
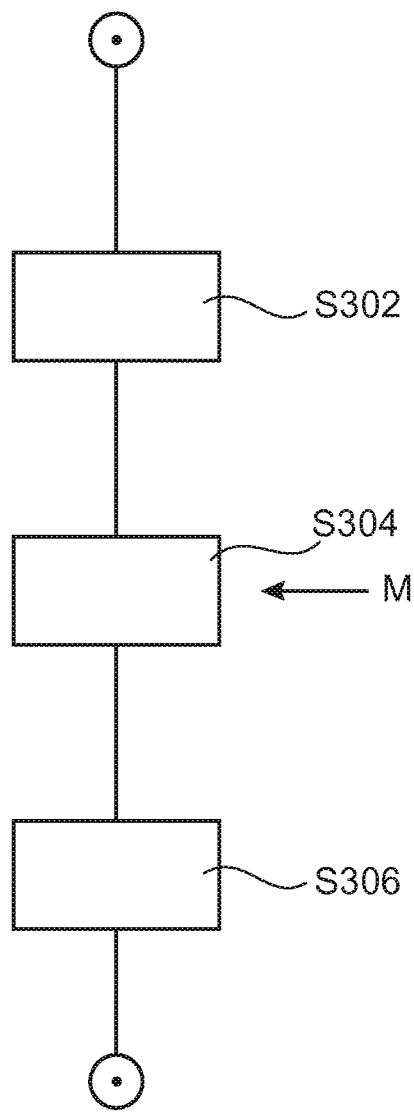
FIG. 3 shows a flow chart of a method of processing detector data.

With reference to FIG. 3, the flowchart shows basic steps of the method as proposed herein.

Step S302 includes receiving the measurement data detected by the multi-bin radiation energy detector during a measurement of radiation that previously interacted with an object of interest. The data detected by the detector during a measurement operation is for an M-fold material decomposition with M≥2 but less than the number of detector bins.

In step S304 the detected measurement data is transformed into radiation attenuation data whilst correcting for a measurement error caused by the detector changing its responsiveness during the measurement operation. The transforming is effected by using a radiation-matter interaction model including:
i) a data parameter that is a parameter for the data detected by the detector bins;
ii) M-fold material decomposition variables; and
iii) a variable for a detector state that causes the change in the detector's responsiveness;
the transformation including solving the model for the material decomposition variables alongside the detector state variable thereby effecting the correction.

In step S306 the solved material decomposition variables are then output as the corrected radiation attenuation data.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computer unit may be adapted to perform or induce a performing of the steps of the method described above. Moreover, it may be adapted to operate the components of the above-described apparatus. The computer unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A detector data processing apparatus comprising:
an input interface (IU) for receiving measurement data detected by a multi-bin radiation energy detector comprising a number of detector bins, the measurement data detected during a measurement of radiation previously interacting with an object of interest, the measurement data detected by the multi-bin radiation energy detector during a measurement operation for an M-fold material decomposition with M≥2 and less than the number of detector bins;
a data transformer (T) comprising a processor configured to transform the detected measurement data into radiation attenuation data whilst correcting for a measurement error caused by the multi-bin radiation energy detector changing its responsiveness during the measurement operation, the data transformer (T) using a radiation-matter interaction model including:
i) a data parameter that is a parameter for the measurement data detected by the detector bins;
ii) M-fold material decomposition variables, $A_1$-$A_m$, each variable representing an attenuation caused by a respective material; and
iii) a variable for a detector state that causes the multi-bin radiation energy detector to change responsiveness;
wherein the data transformer (T) is configured to solve the radiation-matter interaction model for the M-fold material decomposition variables alongside the variable for the detector state thereby effecting a correcting for the measurement error; and
an output unit (OU) configured to output the M-fold material decomposition variables solved by the data transformer as corrected radiation attenuation data.

2. The detector data processing apparatus of claim 1, wherein the data transformer (T) is further configured to output the variable for the detector state.

3. The detector data processing apparatus of claim 1, wherein the radiation-matter interaction model is defined by a system of integral equations each including an integral over an energy spectrum of the radiation previously interacting with an object of interest with each energy spectrum element weighted by an attenuation factor, each equation including at least one selected from a group comprised of the data parameter, the variable for the detector state, and the M-fold material decomposition variables.

4. The detector data processing apparatus of claim 1, wherein the radiation-matter interaction model is defined by a joint probability mass function representing a probability for the detector bins registering a particular measurement event, the joint probability mass function including at least one selected from a group comprised of the data parameter, the variable for the detector state and the M-fold material decomposition variables.

5. The detector data processing apparatus of claim 4, wherein the data transformer (T) is further configured to solve the joint probability mass function for at least one selected from a group comprising the M-fold material decomposition variables and the variable for the detector state by using a maximum-likelihood approach.

6. The detector data processing apparatus of claim 5, wherein solving of the joint probability mass function includes restricting a solution space for the variable for the detector state to functions which satisfy a regularization condition, wherein the regularization condition is enforced by a penalty function.

7. The detector data processing apparatus of claim 6, wherein the penalty function is quadratic.

8. The detector data processing apparatus of claim 4, wherein the joint probability mass function is of a Poison type.

9. The detector data processing apparatus of claim 1, wherein a state of the multi-bin radiation energy detector represents a changing persistent current in a primary converter of the multi-bin radiation energy detector.

10. The detector data processing apparatus of claim 1, wherein a state of the multi-bin radiation energy detector represents the multi-bin radiation energy detector's varying polarization during the measurement operation causing a varying charge collection efficiency of a primary converter of the multi-bin radiation energy detector.

11. An X-ray imaging system comprising:
the detector data processing apparatus according to claim 1; and
the multi-bin radiation energy detector.

12. The X-ray imaging system of claim 11 further including:
a reconstructor (R) configured to reconstruct the corrected radiation attenuation data output by the detector data processing apparatus into one or more images; and
a display for displaying the one or more images.

13. A method of processing detector data, comprising:
receiving measurement data detected by a multi-bin radiation energy detector comprising a number of detector bins, the measurement data detected during a measurement of radiation previously interacting with an object of interest, the measurement data detected by the multi-bin radiation energy detector during a measurement operation for an M-fold material decomposition with M>2 and less than the number of detector bins;
transforming the detected measurement data into radiation attenuation data using a configured processor whilst correcting for a measurement error caused by the multi-bin radiation energy detector changing its responsiveness during measurement operation, the transforming including using a radiation-matter interaction model including:
i) a data parameter that is a parameter for the measurement data detected by the detector bins;
ii) M-fold material decomposition variables, $A_1$-$A_m$, each variable representing an attention caused by a respective material; and
iii) a variable for a detector state that causes the multi-bin radiation energy detector to change responsiveness;
wherein the transforming includes solving the radiation-matter interaction model for the M-fold material decomposition variables alongside the variable for the detector state thereby effecting a correction; and
outputting the M-fold material decomposition variables that are solved with the radiation-matter interaction model as corrected radiation attenuation data.

14. The method according to claim 13, further including:
outputting the variable for the detector state.

15. The method according to claim 13, wherein the radiation-matter interaction model is defined by a system of integral equations each including an integral over an energy spectrum of the radiation previously interacting with an object of interest with each energy spectrum element weighted by an attenuation factor, each equation including at least one selected from a group comprised of the data parameter, the variable for the detector state, and the M-fold material decomposition variables.

16. The method according to claim 13, further including:
reconstructing the corrected radiation attenuation data into one or more images; and
displaying the one or more images on a display.

17. A non-transitory computer readable medium comprising computer program for controlling a computer processing unit, which, when being executed by the computer processing unit is adapted to:
receive measurement data detected by a multi-bin radiation energy detector comprising a number of detector bins, the measurement data detected during a measurement of radiation previously interacting with an object of interest, the measurement data detected by the multi-bin radiation energy detector during a measurement operation for an M-fold material decomposition with M>2 and less than the number of detector bins;
transform the detected measurement data into radiation attenuation data whilst correcting for a measurement error caused by the multi-bin radiation energy detector changing its responsiveness during the measurement operation, the transform includes using a radiation-matter interaction model including:
i) a data parameter that is a parameter for the measurement data detected by the detector bins;
ii) M-fold material decomposition variables, $A_1$-$A_m$, each variable representing an attenuation caused by a respective material; and
iii) a variable for a detector state that causes the multi-bin radiation energy detector to change responsiveness;
wherein the transformation includes solving the radiation-matter interaction model for the M-fold material decomposition variables alongside the variable for the detector state variable thereby effecting a correction; and
output the M-fold material decomposition variables solved by the transformation as corrected radiation attenuation data.

18. The non-transitory computer readable medium comprising computer program for controlling a computer processing unit according to claim 17, which, when being executed by the computer processing unit is further adapted to:
output the variable for the detector state.

19. The non-transitory computer readable medium comprising computer program for controlling a computer processing unit according to claim 17, wherein the radiation-matter interaction model is defined by a system of integral equations each including an integral over an energy spectrum of the radiation previously interacting with an object of interest with each energy spectrum element weighted by an attenuation factor, each equation including at least one selected from a group comprised of the data parameter, the variable for the detector state, and the M-fold material decomposition variables.

20. The non-transitory computer readable medium comprising computer program for controlling a computer processing unit according to claim 17, which, when being executed by the computer processing unit is further adapted to:
reconstruct the corrected radiation attenuation data into one or more images; and
display the one or more images on a display.

* * * * *